US012617763B2

(12) United States Patent
Santoro

(10) Patent No.: US 12,617,763 B2
(45) Date of Patent: May 5, 2026

(54) HYDROBORATION-OXIDATION PROCESS

(71) Applicant: Firmenich SA, Satigny (CH)

(72) Inventor: Francesco Santoro, Satigny (CH)

(73) Assignee: FIRMENICH SA, Satigny (CH)

( * ) Notice: Subject to any disclaimer, the term of this patent is extended or adjusted under 35 U.S.C. 154(b) by 818 days.

(21) Appl. No.: 17/802,994

(22) PCT Filed: Mar. 2, 2021

(86) PCT No.: PCT/EP2021/055205
§ 371 (c)(1),
(2) Date: Aug. 29, 2022

(87) PCT Pub. No.: WO2021/175864
PCT Pub. Date: Sep. 10, 2021

(65) Prior Publication Data

US 2023/0120264 A1 Apr. 20, 2023

(30) Foreign Application Priority Data

Mar. 5, 2020 (EP) .................................... 20161240

(51) Int. Cl.
*C07D 307/83* (2006.01)

(52) U.S. Cl.
CPC .................................. *C07D 307/83* (2013.01)

(58) Field of Classification Search
CPC .................................................... C07D 307/83
See application file for complete search history.

(56) References Cited

U.S. PATENT DOCUMENTS 5,756,857 A 5/1998 Kuribayashi et al.
11,427,554 B2 8/2022 Itoh et al.

FOREIGN PATENT DOCUMENTS

CN 1434014 A 8/2003
CN 109651083 A 4/2019
EP 0 997 330 A1 8/1995
WO 2019198678 A1 10/2019

OTHER PUBLICATIONS

Moreira et al, Enantioselective Synthesis of (2R,3R,7S)-3,7-dimethylpentadecan-2-ol, sex pheromone component of pine saw-flies, 2000, vol. 11, No. 6, p. 614-620. (Year: 2000).*
Jefford et al, Selective, Heterogeneous Oxidation of Alcohols and Diols with Potassium Permanganate, 1988, J. Chem. Soc., Chem. Commun., p. 634-635. (Year: 1988).*
Chavan et al., "A Short and Efficient Synthesis of (−) Mintlactone and (+) iso-Mintlactone", Tetrahedron, 1993, pp. 6429-6436, 49(29).
Ferreira et al., "Pheromone Syntheses: A Tropical Approach. Enantioselective Synthesis of the (2R,6S,10S) and (2S,6S,10S) Isomers of Methyl 2,6,10-Trimethyldodecanoate", Bioorganic & Medicinal Chemistry, 1996, pp. 381-388, 4(3).
Gribble, "Sodium Triacetoxyborohydride", Encyclopedia of Reagents for Organic Synthesis, 2007, pp. 1-11.
Yadav et al., "Synthesis of a key intermediate for the total synthesis of pseudopteroxazole", Tetrahedron, 2010, pp. 1997-2004, 66(11).
Lu et al., "Total synthesis and structural confirmation of the anti-bacterial diterpene leubethanol", Tetrahedron, 2013, pp. 6468-6473, 69(31).
Marshall et al., "The Hydroborating Properties of Sodium Borohydride and Acetic Acid", The Journal of Organic Chemistry, 1963, pp. 595-596, 28(2).
Gaudin, "Synthesis and Organoleptic Properties of p-Menthane Lactones", Tetrahedron, 2000, pp. 4769-4776, 56 (27).

* cited by examiner

*Primary Examiner* — Adam C Milligan
*Assistant Examiner* — Karen Cheng
(74) *Attorney, Agent, or Firm* — Armstrong Teasdale LLP

(57) ABSTRACT

The present invention relates to the field of organic synthesis and, more specifically, it concerns a process for preparing compound of formula (I) by a hydroboration-oxidation reaction of compound of formula (II).

19 Claims, No Drawings

HYDROBORATION-OXIDATION PROCESS

This present application is a U.S. national phase entry under 35 U.S.C. § 371 of PCT Application No. PCT/EP2021/055205, filed Mar. 2, 2021, which claims priority to European Patent Application No. 20161240.5, filed Mar. 5, 2020. The entire contents of these applications are explicitly incorporated herein by this reference.

TECHNICAL FIELD

The present invention relates to the field of organic synthesis and, more specifically, it concerns a process for preparing compound of formula (I) by a hydroboration-oxidation reaction of compound of formula (II).

BACKGROUND OF THE INVENTION 3,6-dimethylhexahydro-1-benzofuran-2(3H)-one is highly valuable perfumery ingredient also known as Koumalactone® or Natactone® (origin: Firmenich SA). Said compounds may be obtained through the hydroboration-oxidation of 5-methyl-2-(prop-1-en-2-yl)cyclohexan-1-ol followed by oxidation with $KMnO_4$. Nevertheless, typical conditions used for the hydroboration such as $NaBH_4$ and $BF_3$-$Et_2O$ generate in the meantime diborane, a highly toxic and explosive compound.

So, there is a need to develop a new approach toward 3,6-dimethylhexahydro-1-benzofuran-2(3H)-one using reagents which may be safer and more easily used at a larger scale while maintaining even increasing the general yield and avoiding the formation of side products.

The present invention allows obtaining compound of formula (I) with high selectivity starting from compound of formula (II) under hydroboration-oxidation conditions wherein the hydroboration is performed in the presence of $MBH_4$ and a carboxylic acid wherein M represents an alkaline metal.

SUMMARY OF THE INVENTION

The invention relates to the hydroboration-oxidation of compound of formula (II) without the formation of toxic and explosive borane allowing the preparation of compound of formula (I) in high yield and in a safer way.

So, the first object of the present invention is process for the preparation of a compound of formula (I)

(I)

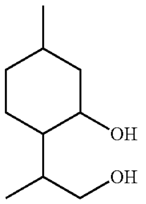

in the form of any one of its stereoisomers or a mixture thereof; comprising the hydroboration—oxidation of compound of the formulae (II)

(II)

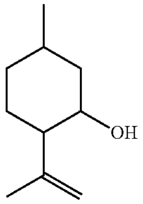

in the form of any one of its stereoisomers or a mixture thereof;

wherein the hydroboration is carried out in the presence of $MBH_4$ and a carboxylic acid wherein M represents an alkaline metal.

A second object of the present invention is a process for preparing a compound of formula (III)

(III)

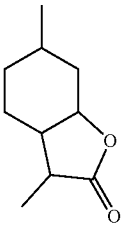

in the form of any one of its stereoisomers or a mixture thereof

Comprising the Steps of i) a hydroboration—oxidation of compound of the formulae (II) into compound of formula (I) as defined in claims 1 to 10 ii) a dehydrogenation/cyclisation of compound of formula (I) into compound of formula (III).

DESCRIPTION OF THE INVENTION

It has now been surprisingly found that the hydroboration of compound of formula (II) may be carried out with $MBH_4$ and a carboxylic acid avoiding the formation of borane. Said conditions allow preparing compound of formula (I) by hydroboration-oxidation conditions while being safe and with a high selectivity toward the Anti-Markovnikov product.

So, the first object of the invention is a process for the preparation of a compound of formula (I)

(I)

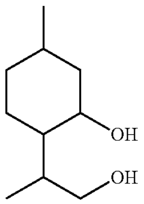

in the form of any one of its stereoisomers or a mixture thereof;

comprising the hydroboration—oxidation of compound of the formulae (II)

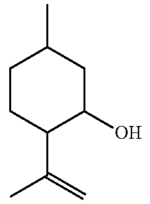

(II)

in the form of any one of its stereoisomers or a mixture thereof;

wherein the hydroboration is carried out in the presence of $MBH_4$ and a carboxylic acid wherein M represents an alkaline metal.

For the sake of clarity, by the expression "any one of its stereoisomers or a mixture thereof", or the similar, it is meant the normal meaning understood by a person skilled in the art, i.e. that the compounds of formula (I) and (II) can be a pure enantiomer or diastereomer. In other words, the compounds of formula (I) and (II) possess several stereocenters and each of said stereocenter can have two different stereochemistries (e.g. R or S). The compounds of formula (I) and (II) may even be in the form of a pure enantiomer or in the form of a mixture of enantiomers or diastereoisomers. The compounds of formula (I) and (II) can be in a racemic form or scalemic form. Therefore, the compounds of formula (I) and (II) can be one stereoisomer or in the form of a composition of matter comprising, or consisting of, various stereoisomers.

According to a particular embodiment, compound of formula (II) is in a racemic form providing a compound of formula (I) in a racemic form. For example, the compound of formula (II) may be (1RS,2SR,5RS)-5-methyl-2-(prop-1-en-2-yl)cyclohexan-1-ol providing compound of formula (I) being (1RS,2SR,5RS)-2-(1-hydroxypropan-2-yl)-5-methylcyclohexan-1-ol; i.e. compound of formula (I) is in the form of a composition of matter comprising, even consisting of, (1RS,2SR,5RS)-2-((S)-1-hydroxypropan-2-yl)-5-methylcyclohexan-1-ol and (1RS,2SR,5RS)-2-((R)-1-hydroxypropan-2-yl)-5-methylcyclohexan-1-ol.

According to another particular embodiment, compound of formula (II) may be in a form of one enantiomer providing compound of formula (I) in a form of two diastereoisomers. The compound of formula (II) is (1R,2S,5R)-5-methyl-2-(prop-1-en-2-yl)cyclohexan-1-ol providing compound of formula (I) being (1R,2S,5R)-2-(1-hydroxypropan-2-yl)-5-methylcyclohexan-1-ol; i.e. compound of formula (I) is in the form of a composition of matter comprising, even consisting of, (1R,2S,5R)-2-((S)-1-hydroxypropan-2-yl)-5-methylcyclohexan-1-ol and (1R,2S,5R)-2-((R)-1-hydroxypropan-2-yl)-5-methylcyclohexan-1-ol.

By the term "hydroboration—oxidation", it is meant the normal meaning in the art; i.e a two-step reaction leading to the anti-Markovnikov hydration of an alkene. This type of conversion is very well known by a person skilled in the art and well documented in any handbook of organic chemistry.

According to any embodiments of the invention, M may be selected form the group consisting of Na, Li or K. In other words, $MBH_4$ may be selected from the group consisting of $NaBH_4$, $LiBH_4$ and $KBH_4$. Particularly, $MBH_4$ may be $NaBH_4$.

$MBH_4$ can be added into the reaction medium of the invention's process in a large range of concentrations. As non-limiting examples, one can cite as $MBH_4$ concentration values those ranging from 1 to 3 equivalents, relative to the total amount of compound of formula (II). In particular, the $MBH_4$ concentration may be comprised between 1 to 2 equivalents, relative to the total amount of compound of formula (II). Even more particularly, the $MBH_4$ concentration may be comprised between 1.1 to 1.5 equivalents, relative to the total amount of compound of formula (II). It goes without saying that the process works also with more $MBH_4$. However, the optimum concentration of $MBH_4$ will depend, as the person skilled in the art knows, on the nature of the latter, on the nature of the solvent, on the temperature and on the desired time of reaction.

According to any embodiments of the invention, the carboxylic acid may be of formula $R(COOH)_n$ wherein n is 1 or 2, R is a hydrogen atom or a $C_{1\_10}$ hydrocarbon optionally substituted by one to five $C_{1-3}$ alkoxy groups, hydroxy groups or halogen atoms.

According to any embodiments of the invention, n is 1 or 2. Particularly, n is 1.

According to any embodiments of the invention, R may be a hydrogen atom or a $C_{1-6}$ hydrocarbon optionally substituted by one to three hydroxy groups or halogen atoms. Particularly, R may be a phenyl group, a $C_{1-5}$ alkyl or alkanediyl group optionally substituted by one to three hydroxy groups or fluorine atoms. When n is 1, R may be a phenyl group or a $C_{1-5}$ alkyl optionally substituted by one to three hydroxy groups or fluorine atoms and when n is 2, R may be a $C_{1-5}$ alkanediyl group optionally substituted by one to three hydroxy groups or fluorine atoms. Even more particularly, R may be a $C_{1-5}$ alkyl group or a phenyl group. Even more particularly, R may be a $C_{1-3}$ alkyl group.

The terms "alkyl" is understood as comprising branched and linear alkyl group.

Non-limiting examples of carboxylic acid may include acetic acid, propionic acid, butyric acid, valeric acid, isovaleric acid, benzoic acid, trifluoroacetic acid, malonic acid, tartaric acid, lactic acid or a mixture thereof. Particularly, the carboxylic acid may be acetic acid.

The carboxylic acid can be added into the reaction medium of the invention's process in a large range of concentrations. As non-limiting examples, one can cite as carboxylic acid concentration values those ranging from 1 to 3 equivalents, relative to the total amount of compound of formula (II). In particular, the carboxylic acid concentration may be comprised between 1 to 2 equivalents, relative to the total amount of compound of formula (II). Even more particularly, the carboxylic acid concentration may be comprised between 1.1 to 1.5 equivalents, relative to the total amount of compound of formula (II). However, the optimum concentration of carboxylic acid will depend, as the person skilled in the art knows, on the nature of the latter, on the nature of the solvent, on the temperature and on the desired time of reaction.

According to any embodiments of the invention, the ratio between $MBH_4$ and the carboxylic acid is 1:1 to 1:2.

According to any embodiments of the invention, the oxidation is carried out in the presence of an oxidizing agent. The person skilled in the art is well aware of oxidizing agent useful in hydroboration-oxidation reaction. Said oxidizing agent useful in hydroboration-oxidation has been widely reported in the scientific literature. Non-limiting examples of oxidizing agent may include hydrogen peroxide, sodium perborate, potassium perborate, sodium percarbonate, potassium percarbonate, peracetic acid, sodium peroxomonosulfate, sodium peroxodisulfate, potassium peroxomonosulfate, potassium peroxodisulfate, sodium hypochlorite or dioxygen. Particularly, the oxidation is carried out in the presence of hydrogen peroxide.

The oxidizing agent can be added into the reaction medium of the invention's process in a large range of concentrations. As non-limiting examples, one can cite as oxidizing agent concentration values those ranging from 1 to 2 equivalents, relative to the total amount of compound of formula (II). In particular, the oxidizing agent concentration may be comprised between 1 to 1.5 equivalents, relative to the total amount of compound of formula (II). It goes without saying that the process works also with more oxidizing agent. However, the optimum concentration of oxidizing agent will depend, as the person skilled in the art knows, on the nature of the latter, on the nature of the solvent, on the temperature and on the desired time of reaction.

According to any embodiments of the invention, the oxidation is performed in a basic media; i.e. the pH is superior to 7, particularly the pH is superior to 10. The oxidation is performed in a presence of a base. The person skilled in the art is well aware of base useful in such oxidation. The base may be an alkaline hydroxide such as NaOH.

The base can be added into the reaction medium of the invention's process in a large range of concentrations. As non-limiting examples, one can cite as base concentration values those ranging from 1.5 to 10 equivalents, relative to the total amount of compound of formula (II). In particular, the base concentration may be comprised between 2 to 5 equivalents, relative to the total amount of compound of formula (II). It goes without saying that the process works also with more base. However, the optimum concentration of base will depend, as the person skilled in the art knows, on the nature of the latter, on the nature of the solvent, on the temperature and on the desired time of reaction.

The temperature of the invention's process may be comprised between 20° C. and 120° C., particularly, in the range comprised between 20° C. and 100° C., more particularly, in the range comprised between 50° C. and 80° C. Of course, a person skilled in the art is also able to select the preferred temperature as a function of the melting and boiling point of the starting and final products as well as the desired time of reaction or conversion.

The invention's process can be carried out in the presence or absence of a solvent. When a solvent is required or used for practical reasons, then any solvent current in hydroboration-oxidation reaction can be used for the purposes of the invention. Non-limiting examples include $C_{6-10}$ aromatic solvents such as toluene or xylene; $C_{5-12}$ hydrocarbon solvents such as hexane or cyclohexane; $C_{4-8}$ ethers such as monoglyme, diglyme, tetrahydrofuran or MTBE; $C_{1-2}$ chlorinated hydrocarbon, such as dichloromethane; or mixtures thereof. In particular, said solvent can be monoglyme or diglyme. The choice of the solvent is a function of the nature of the hydroboration-oxidation conditions and the compound of formula (II), and the person skilled in the art is well able to select the solvent most convenient in each case to optimize the invention's process.

According to any embodiment of the invention, the compound of formula (I) may be further converted to compound of formula (III)

(III)

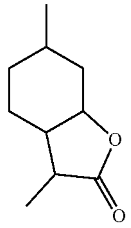

in the form of any one of its stereoisomers or a mixture thereof. Said compound of formula (III) may be obtained by dehydrogenation/cyclisation of compound of formula (I). The person skilled in the art is well aware of the conditions to apply in order to obtain compound of formula (III). Non-limiting examples of suitable dehydrogenation conditions include the one reported in D. Morales-Morales, R. Rédon, Z. Wang, D. W. Lee, C. Yung, K. Magnuson, C. M. Jensen, *Can. J. Chem.* 2001, 79(5-6), 823; C. Gunanathan, D. Milstein, *Science* 2013, 341, 249; D. Spasyuk, S. Smith, D. G. Gusev, *Angew. Chem. Int. Ed.* 2012, 51, 2772; or US2014303374.

According to a particular embodiment, the compound of formula (III) may be (3RS,3aRS,6SR,7aSR)-3,6-dimethylhexahydro-1-benzofuran-2(3H)-one, (3RS,3aSR,6RS,7aRS)-3,6-dimethylhexahydro-1-benzofuran-2(3H)-one or a mixture thereof.

According to a particular embodiment, the compound of formula (III) may be (3S,3aS,6R,7aR)-3,6-dimethylhexahydro-1-benzofuran-2(3H)-one, (3R,3aS,6R,7aR)-3,6-dimethylhexahydro-1-benzofuran-2(3H)-one or a mixture thereof.

Typical manners to execute the invention's process are reported herein below in the examples.

EXAMPLES

The invention will now be described in further detail by way of the following examples, wherein the abbreviations have the usual meaning in the art, the temperatures are indicated in degrees centigrade (° C.). NMR spectra were acquired using either a Bruker Avance II Ultrashield 400 plus operating at 400 MHz, ($^1H$) and 100 MHz ($^{13}C$) or a Bruker Avance III 500 operating at 500 MHz ($^1H$) and 125 MHz ($^{13}C$) or a Bruker Avance III 600 cryoprobe operating at 600 MHz ($^1H$) and 150 MHz ($^{13}C$). Spectra were internally referenced relative to tetramethyl silane 0.0 ppm. $^1H$ NMR signal shifts are expressed in δ ppm, coupling constants (J) are expressed in Hz with the following multiplicities: s, singlet; d, doublet; t, triplet; q, quartet; m, multiplet; b, broad (indicating unresolved couplings) and were interpreted using Bruker Topspin software. $^{13}C$ NMR data are expressed in chemical shift δ ppm and hybridization from DEPT 90 and DEPT 135 experiments, C, quaternary; CH, methine; $CH_2$, methylene; $CH_3$, methyl.

Example 1

Preparation of Compound of Formula (I) Starting from Compound of Formula (II)

A 1.5 L Schmizo reactor, fitted with mechanical stirrer, reflux condenser, and thermometer was connected to a cryostat and flushed with nitrogen. The reflux condenser was connected to a vent that releases the generated hydrogen gas safely. $NaBH_4$ (25 g, 0.66 mmol) and monoglyme (300 g)

were added to the reactor and the suspension was heated to 75° C. while stirring. When the temperature was reached, a previously prepared solution of 5-methyl-2-(prop-1-en-2-yl) cyclohexan-1-ol (100 g, 0.65 mmol) and AcOH (40 g, 0.67 mmol) was added via a syringe-pump in 2 hours. When the addition was completed, the mixture was stirred at 75° C. for 1 h. AcOH (40 g, 0.67 mmol) was added to the mixture in 1 hour, followed by rapid addition of Water (80 g). The biphasic mixture was allowed to decant and the inorganic (bottom) layer was discarded. The stirring was resumed and the temperature was set to 50° C. Aqueous 30% NaOH solution (173 g) was added to the mixture and the pH was measured (pH 14). Then, a solution of $H_2O_2$ 30% was added in 1 hour while keeping the temperature at 50° C. When the addition was complete, the stirring was stopped and the biphasic mixture was allowed to decant. The inorganic layer was discarded and the organic layer was diluted with xylene (100 ml). The solution was concentrated under reduced pressure to eliminate monoglyme and traces of water and 2-(1-hydroxypropan-2-yl)-5-methylcyclohexan-1-ol was precipitated by cooling the remaining solution at 0° C. The colorless crystalline solid was collected by filtration and washed once with cold xylene (95.64 g, 86% yield).

The invention claimed is:

1. A process for the preparation of a compound of formula (I)

(I)

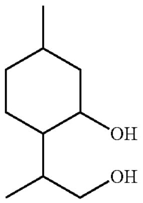

in the form of any one of its stereoisomers or a mixture thereof, said process comprising the hydroboration—oxidation of a compound of formula (II)

(II)

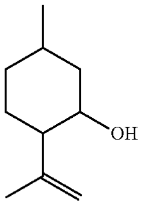

in the form of any one of its stereoisomers or a mixture thereof, wherein the hydroboration is carried out in the presence of $MBH_4$ and a carboxylic acid wherein M represents an alkaline metal.

2. The process according to claim 1, wherein $MBH_4$ is selected from the group consisting of $NaBH_4$, $LiBH_4$ and $KBH_4$.

3. The process according to claim 1, wherein the carboxylic acid is of formula $R(COOH)_n$ wherein n is 1 or 2, R is a hydrogen atom or a $C_{1-10}$ hydrocarbon optionally substituted by one to five $C_{1-3}$ alkoxy groups, hydroxy groups or halogen atoms.

4. The process according to claim 1, wherein R is a $C_{1-5}$ alkyl group or a phenyl group and n is 1.

5. The process according to claim 1, wherein the carboxylic acid is acetic acid, propionic acid, butyric acid, valeric acid, isovaleric acid, benzoic acid, trifluoroacetic acid, malonic acid, tartaric acid, lactic acid or a mixture thereof.

6. The process according to claim 1, wherein the ratio between $MBH_4$ and the carboxylic acid is 1:1 to 1:2.

7. The process according to claim 1, wherein the oxidation is carried out in the presence of hydrogen peroxide, sodium perborate, potassium perborate, sodium percarbonate, potassium percarbonate, peracetic acid, sodium peroxomonosulfate, sodium peroxodisulfate, potassium peroxomonosulfate, potassium peroxodisulfate, sodium hypochlorite or dioxygen.

8. The process according to claim 1, wherein compound of formula (I) is (1R,2S,5R)-2-(1-hydroxypropan-2-yl)-5-methylcyclohexan-1-ol.

9. The process according to claim 1, wherein compound of formula (II) is (1R,2S,5R)-5-methyl-2-(prop-1-en-2-yl) cyclohexan-1-ol.

10. The process according to claim 1, wherein the oxidation is performed in a presence of base.

11. A process for preparing a compound of formula (III)

(III)

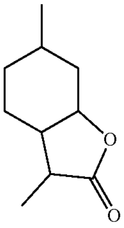

in the form of any one of its stereoisomers or a mixture thereof, said process comprising i) a hydroboration—oxidation of a compound of formulae (II) into a compound of formula (I) as defined in claim 1; and ii) a dehydrogenation/cyclisation of the compound of formula (I) into compound of formula (III).

12. The process according to claim 2, wherein the carboxylic acid is acetic acid, propionic acid, butyric acid, valeric acid, isovaleric acid, benzoic acid, trifluoroacetic acid, malonic acid, tartaric acid, lactic acid or a mixture thereof.

13. The process according to claim 12, wherein the ratio between $MBH_4$ and the carboxylic acid is 1:1 to 1:2.

14. The process according to claim 12, wherein the carboxylic acid is of formula $R(COOH)_n$ wherein n is 1 or 2, R is a hydrogen atom or a $C_{1-10}$ hydrocarbon optionally substituted by one to five $C_{1-3}$ alkoxy groups, hydroxy groups or halogen atoms.

15. The process according to claim 14, wherein R is a $C_{1-5}$ alkyl group or a phenyl group and n is 1.

16. The process according to claim 12, wherein the oxidation is performed in a presence of base.

17. The process according to claim 12, wherein the oxidation is carried out in the presence of hydrogen peroxide, sodium perborate, potassium perborate, sodium percarbonate, potassium percarbonate, peracetic acid, sodium peroxomonosulfate, sodium peroxodisulfate, potassium peroxomonosulfate, potassium peroxodisulfate, sodium hypochlorite or dioxygen.

18. The process according to claim 15, wherein the oxidation is performed in a presence of base.

19. The process according to claim 15, wherein the oxidation is carried out in the presence of hydrogen peroxide, sodium perborate, potassium perborate, sodium percarbonate, potassium percarbonate, peracetic acid, sodium peroxomonosulfate, sodium peroxodisulfate, potassium peroxomonosulfate, potassium peroxodisulfate, sodium hypochlorite or dioxygen.

* * * * *